US00PP37260P2

(12) United States Plant Patent
Boxriker

(10) Patent No.: US PP37,260 P2
(45) Date of Patent: Feb. 10, 2026

(54) ***DIANTHUS* PLANT NAMED 'KLEDP25525'**

(50) Latin Name: ***Dianthus* x *caryophyllus* L. hort.**
Varietal Denomination: KLEDP25525

(71) Applicant: KLEMM + SOHN GMBH & CO. KG, Stuttgart (DE)

(72) Inventor: Maike Boxriker, Stuttgart (DE)

(73) Assignee: Klemm + Sohn Gmbh & Co., KG, Stuttgart (DE)

( * ) Notice: Subject to any disclaimer, the term of this patent is extended or adjusted under 35 U.S.C. 154(b) by 0 days.

(21) Appl. No.: 19/188,617

(22) Filed: Apr. 24, 2025

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./278, 273
CPC ..... A01H 5/0233
See application file for complete search history.

(56) References Cited

PUBLICATIONS https://www.floraldaily.com/article/9718016/cast-day-3-good-weather-steady-guests-and-amazing-plants/; Mar. 27, 2025; 4 pages.*
https://www.selectanorthamerica.com/SpringPlants/SeriesInfo/?phid=022506574036363; Jun. 11, 2025; 1 page.*
https://www.facebook.com/photo?fbid=1185679080228339&set=a.471070471689207; Mar. 16, 2025; 1 page.*
https://selecta-one.com/katalog/catalogs/Dianthus_2025_NE/pdf/complete.pdf; 2025; 3 pages.*
In re Wingen; Feb. 2, 2023; 9 pages.*

* cited by examiner

*Primary Examiner* — Kent L Bell
(74) *Attorney, Agent, or Firm* — Weatherly IP Solutions, LLC; James Weatherly; Karen Bechtold

(57) ABSTRACT

A new *Dianthus* plant designated 'KLEDP25525' particularly distinguished by bicolored flowers with dark red centers and white along the edge of the petals; and tall, upright plants with shorter flower stems on top, is disclosed.

1 Drawing Sheet

Genus and species: *Dianthus* x *caryophyllus* L. hort.
Variety denomination: 'KLEDP25525'.

BACKGROUND OF THE NEW PLANT

The present invention comprises a new and distinct variety of *Dianthus*, botanically known as *Dianthus* x *caryophyllus* L. hort. and hereinafter referred to by the variety name 'KLEDP25525'. In 2018 a whole plant mutation was identified within a group of *Dianthus* 'KLEDP07089' at a plant production facility in the Netherlands and the plant was subsequently shipped to Stuttgart, Germany. The mutation was evaluated and selected for by the inventor in Stuttgart, Germany and named 'KLEDP25525'. In May 2018, 'KLEDP25525' was first vegetatively propagated by vegetative stem cuttings in Stuttgart, Germany. 'KLEDP25525' was found to reproduce true to type in successive generations of asexual propagation in Stuttgart, Germany via vegetative cuttings.

SUMMARY

The following are the most outstanding and distinguishing characteristics of 'KLEDP25525' when grown under normal horticultural practices in Stuttgart, Germany.

1. Bicolored flowers with dark red centers and white along the edge of the petals; and
2. Tall, upright plants with shorter flower stems on top.

DESCRIPTION OF THE PHOTOGRAPH

This new *Dianthus* plant is illustrated by the accompanying photograph of an 11-week-old plant taken in March 2023 and grown in a greenhouse in Stuttgart, Germany. The colors shown are as true as can be reasonably obtained by conventional photographic procedures. The photograph is a whole plant photograph of 'KLEDP25525' and shows the foliage, buds, and flowers.

DESCRIPTION

The following detailed descriptions set forth the distinctive characteristics of 'KLEDP25525'. The data which define these characteristics were collected from asexual reproductions carried out in Stuttgart, Germany. Data was collected in May 2024 from plants potted in week 41 of 2021 grown in a greenhouse. Color references are to The R.H.S. Colour Chart of The Royal Horticultural Society of London (R.H.S.), $5^{th}$ edition (2007).

Classification:
*Family.*—Caryophyllaceae.
*Botanical.*—*Dianthus caryophyllus* L. hort.
*Designation.*—'KLEDP25525'.
*Type.*—Pot carnation.

Parentage:
*Parent.*—*Dianthus* 'KLEDP07089'. (unpatented).

Plant:
*Propagation type.*—Vegetative cuttings via stem.
*Time to produce a rooted young plant.*—28 days.
*Root description.*—Fine roots, young roots are RHS 155C.
*Rooting habit shape.*—Lanceolate.
*Plant form.*—Upright.

*Plant height.*—11 cm.
*Plant diameter or spread.*—20 cm.

Lateral branches/stems:
*Shape of the branch in cross-section.*—Circular.
*Hollowness of the branch.*—Absent.
*Length.*—10.5 cm.
*Diameter.*—0.2 cm.
*Internode length.*—2.3 cm.
*Internode quantity per branch.*—7.
*Number of internodes per branch/stem.*—7.
*Node length.*—0.4 cm.
*Node diameter.*—0.3 cm.
*Texture.*—Smooth.
*Color.*—RHS 137B.
*Flower clustering on the lateral branch.*—In some lateral branches.
*Stem thickness.*—Medium.

Foliage:
*Arrangement.*—Opposite.
*Length.*—6.7 cm.
*Width.*—1.0 cm.
*Shape.*—Obovate.
*Apex.*—Acute.
*Base.*—Obtuse.
*Margin.*—Entire.
*Texture (both upper and lower surfaces).*—Smooth.
*Cross-section of the leaf.*—Moderately concave.
*Curvature of the leaf.*—Absent.
*Glaucosity of the leaf.*—Weak.
*Leaf color (both immature and mature).*—Immature: Upper surface: RHS 137B. Lower surface: RHS 137C. Mature: Upper surface: RHS N137A. Lower surface: RHS N137C.
*Venation pattern.*—Absent.

Flowers:
*Flower type and habit.*—Semi-double and round.
*Fragrance.*—Present, fresh and sweet.
*Position of the flowers compared to the foliage of the plant.*—Same level.
*Profile of both the upper and lower part in the lateral view.*—Flat.
*Diameter of the flower.*—3.6 cm.
*Natural flowering season.*—Spring to autumn.
*Number of flowers per spray.*—3 to 4.
*Flower longevity on the plant.*—14 days.

Buds:
*Length.*—2.1 cm.
*Diameter.*—1.0 cm.
*Shape.*—Oblong.
*Color.*—RHS 137A.
*Extrusion of the styles at the bud stage.*—Absent.

Corolla:
*Quantity of petals and arrangement.*—27 and arranged in several whorls.
*Corolla height.*—1.0 cm.
*Petal length.*—2.8 cm.
*Petal width.*—1.3 cm.
*Petal shape.*—Obtuse.
*Petal apex.*—Obtuse.
*Petal base.*—Acute.
*Petal margin.*—Crenate.
*Depth of petal margin.*—Shallow.
*Petal texture (both upper and lower surfaces).*—Smooth.
*Petal color.*—Immature: Upper surface: RHS 59A main color with RHS N155C along the petal edge and at the petal base. Lower surface: RHS 59C. Mature: Upper surface: RHS 61A main color with RHS N155C along the petal edge and at the petal base. Lower surface: RHS 59C.
*Macule.*—Absent.

Calyx:
*Quantity of sepals and arrangement.*—Composed of 5 sepals.
*Longitudinal axis of the lobes of the calyx.*—Straight.
*Shape.*—Acute.
*Calyx height.*—2.0 cm.
*Calyx diameter (at the apex).*—0.4 cm.
*Sepal texture (both upper and lower surfaces).*—Smooth.
*Sepal color.*—Upper surface: RHS 137A. Lower surface: RHS 138C.
*Position of the outer lobes of the epicalyx in relation to the calyx.*—Free.
*Apex shape of the outer lobes of the epicalyx.*—Acute.
*Tip length of the outer lobes of the epicalyx.*—Less than 0.1 cm.
*Apex shape of the inner lobes of the epicalyx.*—Short acuminate.
*Tip length of the inner lobes of the epicalyx.*—0.3 cm.

Peduncles:
*Length.*—1 cm.
*Diameter.*—0.2 cm.
*Strength.*—Strong.
*Texture.*—Smooth.
*Color.*—RHS 137A.

Reproductive organs:
*Stamens.*—Quantity per flower: 6. Filament length: 1.1 cm. Filament color: RHS 157C. Anther length: 0.3 cm. Anther diameter: 0.1 cm. Anther color: RHS 165C. Pollen amount: None observed.
*Pistils.*—Quantity per flower: 3. Length: 0.2 cm. Diameter: 0.1 cm. Stigma: Color: RHS NN155B. Shape: Filamentous. Length: 0.1 cm. Diameter: 0.1 cm.
*Style.*—Color: RHS NN155B. Length: 1.0 cm. Diameter: 0.1 cm. Shoulder: Absent. Number of styles: 3.
*Ovary.*—Color: RHS145B. Width: 0.5 cm. Texture: Smooth.

Seeds: None observed to date.

Disease and insect resistance: No particular disease or insect resistance observed.

COMPARISON OF 'KLEDP25525' WITH PARENTAL LINE AND KNOWN VARIETY

'KLEDP25525' is distinguished from the parent as described in Table 1.

TABLE 1

Comparison with Parental Line

| Characteristic | 'KLEDP25525' | Parent 'KLEDP07089' |
|---|---|---|
| Flower color and pattern | Dark red bicolor petal with white base and white border | Pink and maculated |

'KLEDP25525' can be compared to the commercial *Dianthus* variety 'KLEDP07088' (unpatented). Differences between the varieties are described in Table 2.

TABLE 2

| Comparison with Similar Variety | | |
|---|---|---|
| Characteristic | 'KLEDP25525' | 'KLEDP07088' |
| Flower color | Dark red bicolor petal with white base and white border | Purple and white |
| Habit | Upright with shorter flower stems on top | Upright with longer flower stems |

TABLE 2-continued

| Comparison with Similar Variety | | |
|---|---|---|
| Characteristic | 'KLEDP25525' | 'KLEDP07088' |
| Earliness | Medium earliness but later than 'KLEDP07088' | Earlier flowering than 'KLEDP25525' |

I claim:

1. A new and distinct variety of *Dianthus* plant named designated 'KLEDP25525' as illustrated and described herein.

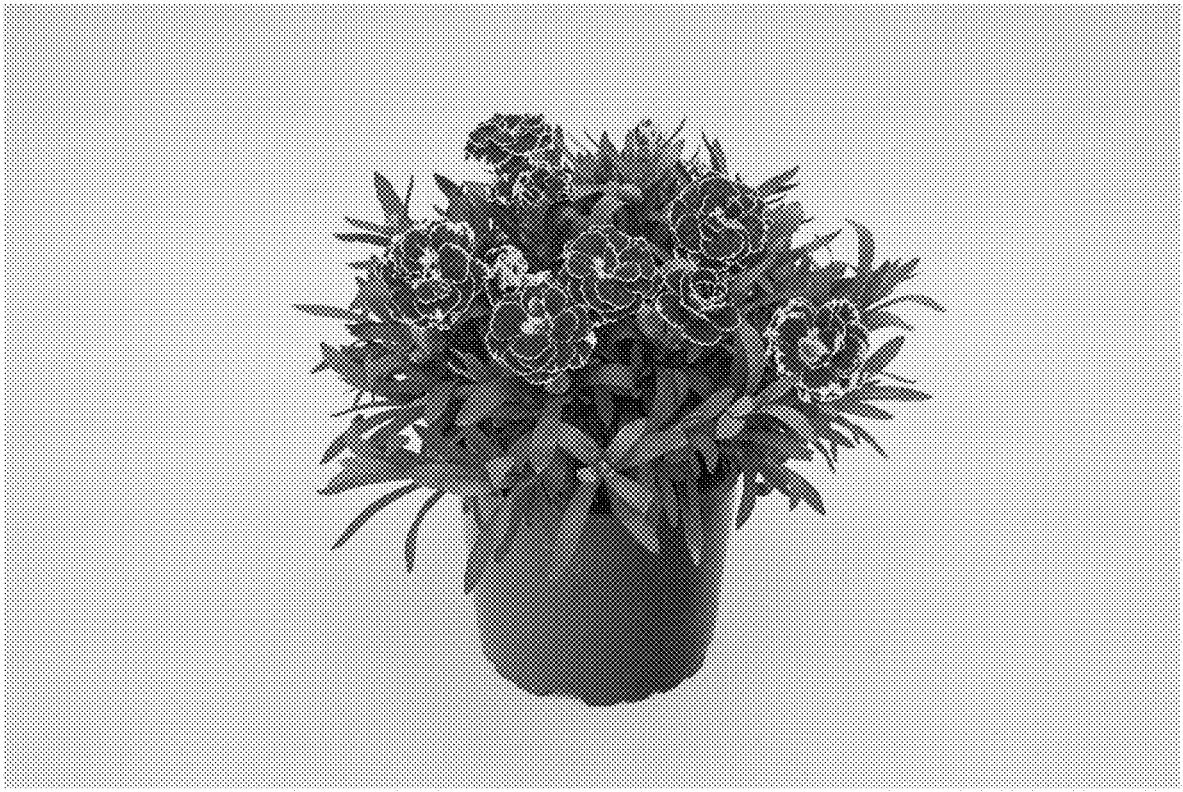

* * * * *